(12) United States Patent
Flora et al.

(10) Patent No.: US 7,165,453 B2
(45) Date of Patent: Jan. 23, 2007

(54) FLEXIBLE ELECTROMAGNETIC ACOUSTIC TRANSDUCER SENSOR

(75) Inventors: John Flora, Lynchburg, VA (US); Muhammad Ali, Lynchburg, VA (US); Grady Powers, Lynchburg, VA (US)

(73) Assignee: Electric Power Research Institute, Palo Alto, CA (US)

( * ) Notice: Subject to any disclaimer, the term of this patent is extended or adjusted under 35 U.S.C. 154(b) by 0 days.

(21) Appl. No.: 11/185,143

(22) Filed: Jul. 20, 2005

(65) Prior Publication Data

US 2006/0027022 A1 Feb. 9, 2006

Related U.S. Application Data

(60) Provisional application No. 60/590,636, filed on Jul. 23, 2004.

(51) Int. Cl.
*G01N 29/04* (2006.01)
*G01N 29/00* (2006.01)
*H04R 15/00* (2006.01)

(52) U.S. Cl. ......................................... 73/643; 367/168
(58) Field of Classification Search ................. 73/643, 73/644, 642, 627, 622, 635, 636, 637, 638, 73/639; 367/140, 168
See application file for complete search history.

(56) References Cited

U.S. PATENT DOCUMENTS

| | | | | |
|---|---|---|---|---|
| 3,674,946 A | * | 7/1972 | Winey | ......................... 381/408 |
| 3,944,963 A | | 3/1976 | Hively | |
| 4,049,954 A | | 9/1977 | Da Costa Vieira et al. | |
| 4,058,002 A | * | 11/1977 | Moran | ......................... 73/620 |
| 4,070,762 A | | 1/1978 | Siddall | |
| 4,102,207 A | * | 7/1978 | Frost et al. | ................... 73/643 |
| 4,170,142 A | | 10/1979 | Posakony et al. | |
| 4,195,530 A | | 4/1980 | Ross et al. | |
| 4,203,069 A | | 5/1980 | Davis | |
| 4,210,028 A | | 7/1980 | Hildebrand | |
| 4,248,092 A | | 2/1981 | Vasile et al. | |
| 4,290,308 A | | 9/1981 | Dau | |
| 4,296,486 A | * | 10/1981 | Vasile | ......................... 367/140 |
| 4,303,885 A | | 12/1981 | Davis et al. | |
| 4,305,661 A | | 12/1981 | Pryor et al. | |
| 4,307,612 A | | 12/1981 | Elsley et al. | |
| 4,320,661 A | | 3/1982 | Peterson et al. | |
| 4,391,532 A | | 7/1983 | Hara | |
| 4,393,711 A | | 7/1983 | Lapides | |
| 4,403,860 A | | 9/1983 | Pryor | |
| 4,428,237 A | | 1/1984 | Zeger et al. | |
| 4,432,931 A | | 2/1984 | Lockett | |
| 4,434,663 A | * | 3/1984 | Peterson et al. | .............. 73/643 |
| 4,526,037 A | | 7/1985 | Wentzell et al. | |
| 4,546,314 A | | 10/1985 | Minerbo et al. | |

(Continued)

*Primary Examiner*—Helen Kwok
(74) *Attorney, Agent, or Firm*—Curatolo Sidoti Co., LPA; Joseph G. Curatolo; Salvatore A. Sidoti

(57) ABSTRACT

An array of magnets designed of flexible components and materials can be easily shaped to fit to the contour of various curved surfaces and structures. EMATs that incorporate these magnets, in addition to being flexible, may be smaller in volume than the conventional EMAT magnets and therefore easier to apply to complex structures where access may be restricted. Also, flexible multiple-pole magnet arrays can be easily and economically fabricated in various shapes and configurations, thereby increasing versatility, utility and cost effectiveness in comparison to the rigid, conventional magnet designs.

18 Claims, 5 Drawing Sheets

U.S. PATENT DOCUMENTS

| | | |
|---|---|---|
| 4,546,315 A | 10/1985 | Minerbo et al. |
| 4,744,661 A | 5/1988 | Ulbers et al. |
| 4,982,158 A | 1/1991 | Nakata et al. |
| 5,023,549 A | 6/1991 | Dau et al. |
| 5,237,874 A | 8/1993 | Latimer et al. |
| 5,359,898 A * | 11/1994 | Latimer ..................... 73/600 |
| 5,608,691 A | 3/1997 | MacLauchlan et al. |
| 5,691,476 A * | 11/1997 | Madaras ..................... 73/644 |
| 5,698,787 A | 12/1997 | Parzuchowski et al. |
| 5,705,741 A | 1/1998 | Eaton et al. |
| 5,717,169 A | 2/1998 | Liang et al. |
| 5,734,588 A | 3/1998 | Rose et al. |
| 5,825,017 A | 10/1998 | Pryor |
| 5,837,898 A | 11/1998 | MacLauchlan |
| 6,070,467 A | 6/2000 | Rosenberg et al. |
| 6,082,198 A | 7/2000 | Sabourin et al. |
| 6,109,108 A | 8/2000 | Ohtani et al. |
| 6,176,132 B1 | 1/2001 | MacLauchlan |
| 6,188,643 B1 | 2/2001 | Liang et al. |
| 6,215,836 B1 | 4/2001 | Walker et al. |
| 6,282,964 B1 | 9/2001 | Hancock et al. |
| 6,449,326 B1 | 9/2002 | Walker et al. |
| 6,578,424 B1 | 6/2003 | Ziola et al. |
| 6,666,095 B1 | 12/2003 | Thomas et al. |
| 6,736,011 B1 | 5/2004 | Zayicek et al. |
| 6,766,694 B1 * | 7/2004 | Hubschen ..................... 73/643 |
| 6,935,036 B1 | 8/2005 | Raab et al. |

* cited by examiner

FLEXIBLE ELECTROMAGNETIC ACOUSTIC TRANSDUCER SENSOR

This application claims the benefit of the filing date of U.S. Provisional Application for Patent Ser. No. 60/590,636 filed Jul. 23, 2004, which is incorporated herein by reference.

FIELD OF THE INVENTION

Electromagnetic acoustic transducers (EMATs) comprising flexible magnets that conform to the surface of the object to which they are applied, thereby providing superior performance at reduced cost of fabrication compared to conventional EMAT designs that are composed of rigid and expensive components.

BACKGROUND

Electromagnetic acoustic transducers (EMATs) are electrical devices that can transmit and receive sound waves in electrically conducting materials without requiring contact with the material. Since sound waves reflect from defects such as cracks and voids, EMATs are typically used as inspection devices. The characteristics of the sound waves transmitted from and received by EMATs, including frequency, intensity, mode and beam shape are determined primarily by the EMAT design and electrical excitation of the EMAT components.

EMATs offer several advantages when compared to piezoelectric transducers. EMATs do not require any fluid coupling, unlike piezoelectric transducers in which the sound is produced in the probe and transferred to the material through a coupling medium such as oil or water. EMATs can inspect at greater speeds and therefore provide greater throughput when they are used in automated inspection systems. Since EMATs generate sound waves immediately below the surface of the material being tested, they provide greater accuracy, reliability and repeatability for applications in which the material is contaminated, rough, heated to elevated temperatures or moving at high speeds. Since fabrication of EMATs can be very precise, the EMAT or its components can be interchanged with minimal variation in characteristics or performance. The simple construction of EMATs provides a nearly unlimited variety of designs to facilitate shaping, steering and focusing beams to achieve the desired acoustic effects.

EMATs are typically composed of two fundamental components: magnets and coils of insulated electrical conductors. Either permanent magnets or electromagnets (magnets) are used to produce magnetic fields that penetrate the surface of the material component being tested. Coils composed of electrical conductors, commonly referred to as RF coils, are placed between the magnets and the test material. These RF coils are used to induce high frequency magnetic fields in the test material. Interaction between the fields from the magnet and the fields from the RF coils produce forces within the atomic or molecular lattice of the test material. The forces vary in intensity and direction with time at frequencies equal to those of the current in the RF coils. The oscillating forces produce acoustic or sound waves that normally propagate within the test material and away from the EMAT in two opposing directions.

Illustrated in FIG. 1 is an EMAT configuration that is used to generate vertically polarized shear (SV) waves, Lamb waves and surface waves, which are also referred to as Raleigh waves. A magnet 1 produces a magnetic field 2 perpendicular to the metal part under test, or the test material 3. A meander radio frequency (RF) coil 4 illustrated by but not limited to a meander coil composed of insulated electrical conductors is energized by an alternating power source 5, and results in alternating current 6 which flows in the RF coil 4 between its terminals. The alternating current 6 produces alternating fields 7, which encircle the eddy currents 8 and penetrate the surface of the test material 3. The penetrating alternating fields 7 induce alternating eddy currents 8 in and near the surface of the test material 3. Alternating magnetic fields 9, which encircle the eddy currents 8, are also generated in the test material 3. The alternating fields 7 from the eddy currents 8 interact with the alternating magnetic fields 9 from the magnet 1 to produce Lorentz forces 10, in the test material 3 and under each RF coil 4. These Lorentz forces 10 result in sound waves, such as horizontally polarized shear waves, which are ultrasonic acoustic or sound waves commonly known in the art as SH waves 11, which propagate from the EMAT in opposite directions in the test material 3.

Illustrated in FIG. 2 is an EMAT which uses a magnet array 12 such as an array of permanent magnets and an encircling RF coil 4 to generate SH waves 11. Part of the RF coil 4 is under the magnet array 12, and also in close proximity to the test material 3. When an alternating power source 5 is applied to the RF coil 4, eddy currents 8 and the associated alternating magnetic fields 9 are induced in the test material 3. Interaction of the magnetic fields 2 from the magnet array 12 and the alternating fields 7 from the eddy currents 8 produce Lorentz forces 10 in the test material 3, which are near the surface and also parallel to the surface of the test material 3. These Lorentz forces 10 result in SH waves 11 that propagate in opposite directions in the test material 3.

Illustrated in FIG. 3 is an EMAT, which uses a magnet 1 such as an electromagnet and RF coils 4 to produce SH waves 11 in some ferromagnetic materials 14 that exhibit the property of magnetostriction. A magnet coil 13 composed of insulated, electrical conductors is wound around a core of ferromagnetic material 14. When the magnet coil 13 is excited by electrical power source 15, a transient current 16 flows between the terminals of the magnet coil 13. The transient current 16 in turn generates a tangential magnetic field 17, a part of which penetrates the surface of the test material 3. The tangential magnetic field 17 induces transient eddy currents 18, which flow under and around the poles of the magnet 1.

RF coil 4 is excited by alternating current 6 at frequencies that are greater than the component frequencies of the transient current 16 of the magnet coil 13. Alternating current 6 in the RF coil 4 induces alternating eddy currents 8 and associated magnetic fields 9 in the test material 3. When the test material 3 exhibits the physical property of magnetostriction, the vector summation of the resultant magnetic fields 9 induced by the RF coil 4 and the tangential magnetic fields 17 induced by the magnet 1, cause expansion and contraction of the test material 3. Alternating expansion and contraction of the test material results in propagation of SH waves 11 from the EMAT in two directions.

SUMMARY

An array of magnets designed of flexible components and materials can be easily shaped to fit to the contour of various curved surfaces and structures. EMATs that incorporate these magnets, in addition to being flexible, may be smaller in volume than the conventional EMAT magnets and therefore easier to apply to complex structures where access may be restricted. Also, the flexible magnet arrays can be easily and economically fabricated in various shapes and configurations, thereby increasing versatility, utility and cost effectiveness in comparison to the rigid, conventional magnet designs.

An electromagnetic acoustic transducer is provided, adapted to conform to the surface of a non-planar test substrate.

In certain embodiments, the electromagnetic acoustic transducer comprises an array of magnets conformable to the non-planar test substrate surface, wherein the magnets contain magnetic poles and interconnecting segments.

In one embodiment, the array of magnets comprises a flexible compound containing particles of ferromagnetic material, wherein electrical conductors are disposed between the magnetic poles capable of generating magnetic fields perpendicular to the faces of each magnetic pole when conducting current.

In another embodiment, the array of magnets comprises a flexible compound containing particles of permanent magnet material, wherein the magnetic poles are optionally magnetized to provide static magnetic fields perpendicular to the face of each magnetic pole.

A method of interrogating a test substrate having a non-planar surface is provided using the electromagnetic acoustic transducer comprising:

conforming the electromagnetic acoustic transducer to the surface of the test substrate in monitoring proximity to the surface, generating a sound wave by interaction of fields from the electromagnetic acoustic transducer magnet and electrical conductor, and, detecting at least one characteristic of the sound wave reflected by the test substrate.

DETAILED DESCRIPTION

Electromagnetic acoustic transducers (EMATs) can be easily shaped during or after fabrication so that the EMATs can be used to interrogate components and structures having curved surfaces without substantial loss of signal response to defects or properties of these components and structures that could otherwise be caused by poor compliance of the EMAT to the surface of the test material. The EMATs comprise primarily two component parts: magnets and electrical conductors which provide RF signals such as RF coils. The magnets may be comprised of one or more cores of ferromagnetic material and electrical conductors.

An EMAT is disclosed which comprises a magnet or a flexible multiple-pole magnet array which contains materials designed, fabricated and integrated with electrical conductors which provide RF signals such as RF coils. The EMAT can be easily shaped during or after fabrication so that it can be used to interrogate components and structures having curved surfaces. This substantially reduces the loss of signal response to the defects or properties of these components and structures caused by poor compliance and decrease in proximity of the EMAT to the surface of the test material or substrate.

The flexible multiple-pole magnet array may be formed in rows wherein each row has a radius of curvature about a point or points so as to provide focusing of the generated SH waves in a test material component. The array of magnets may have variation in the distance between adjacent magnetic poles that is a function of the radial distance from the focal point. This variation in the array of magnets causes a change in the vertical width of the SH wave. In other embodiments, two or more arrays of magnets may be arranged in tandem with each having a different radial distance between magnetic poles so that they will have approximately the same SH wave angle and focal point when operated within a prescribed range of frequencies. In a further embodiment, the array of magnets may have high frequency (RF) conductors embedded in grooves which lie across the magnetic pole faces and are collinear with radial projections from the focal point.

A flexible multiple-pole magnet array may comprise an array of magnets and magnetic poles fabricated at least in part from a flexible material such as silicone rubber containing particles of ferromagnetic material such as iron, or permanent magnet material such as neodymium iron boron.

Electrical conductors may have a shape, width and thickness such that they can be installed between the magnet poles and energized with an electrical current to provide alternating magnetic polarity between adjacent magnetic poles. In other embodiments, the electrical conductors may have a shape, width and thickness such that they can be installed between the magnet poles in multiple layers, connected in series and energized electrically to provide alternating magnetic polarity between adjacent poles.

Figure 1:
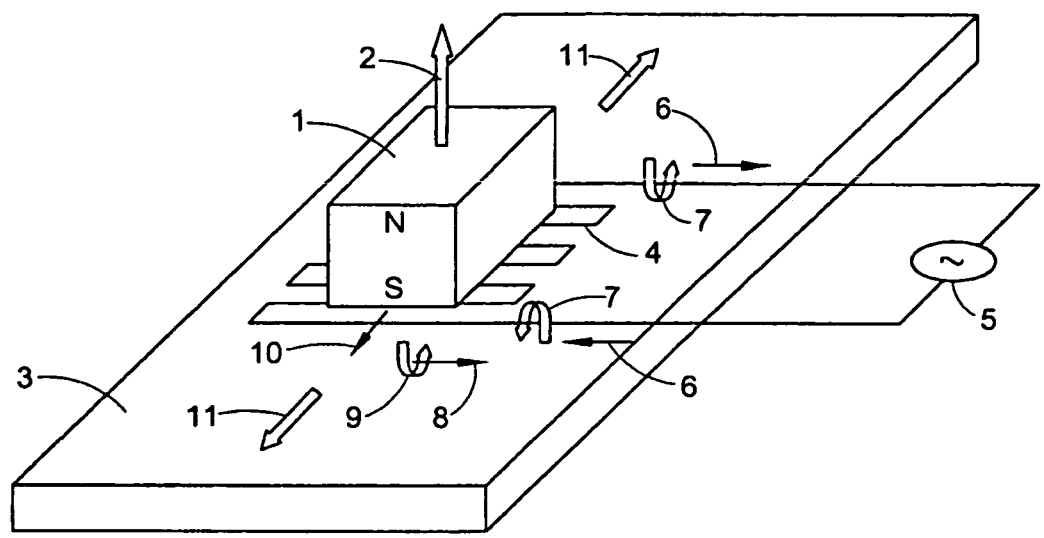
FIG. 1 illustrates an EMAT comprising a permanent magnet and an RF coil for generation and detection of SH waves, Lamb waves and surface waves in electrically conducting materials.
Figure 2:
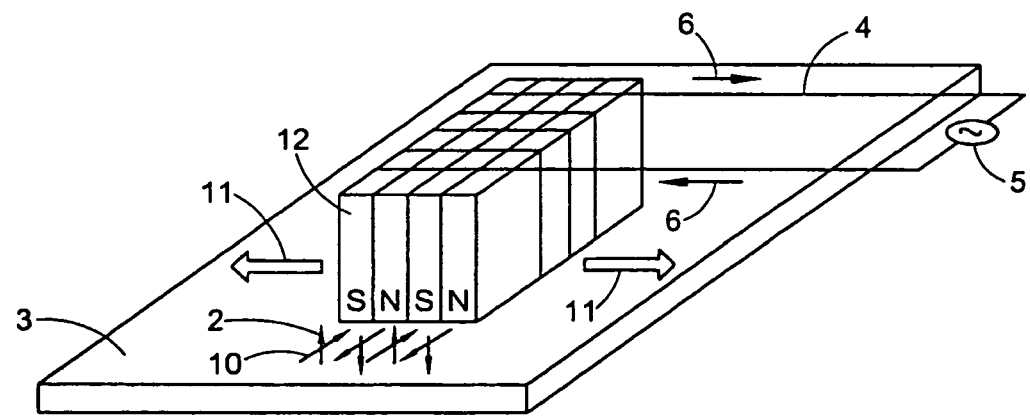
FIG. 2 illustrates an EMAT comprising an array of permanent magnets and an RF coil for generation and detection of horizontally polarized shear waves.
Figure 3:
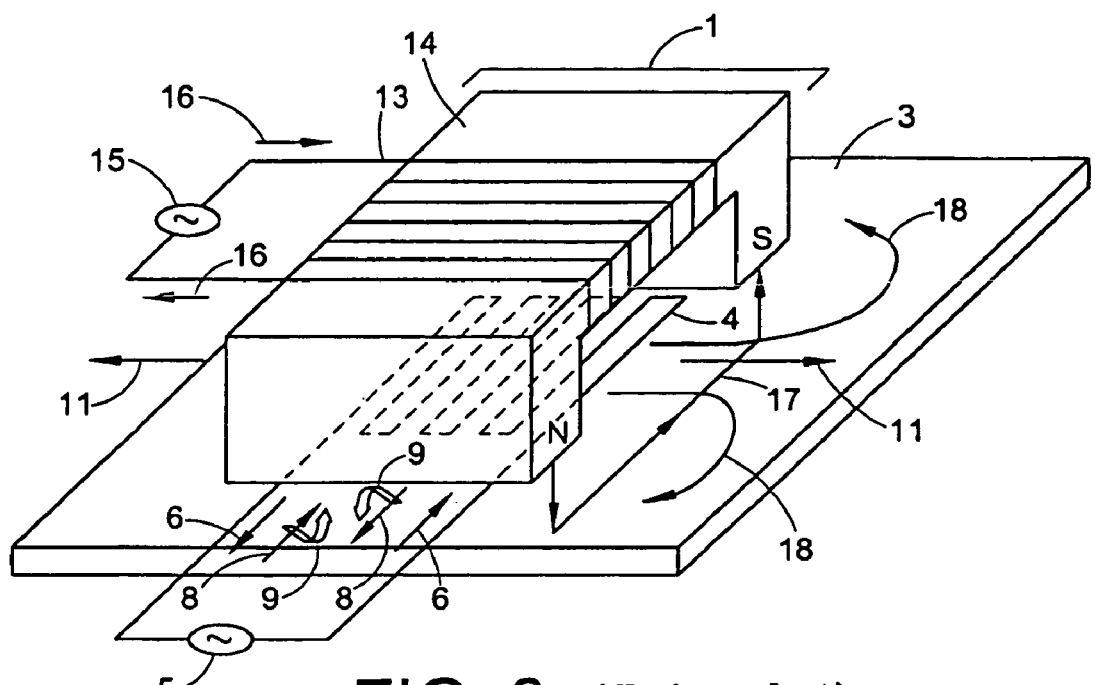
FIG. 3 illustrates an EMAT comprising an electromagnet and meander RF coil for generation of horizontally polarized SH waves in ferromagnetic materials that exhibit magnetostriction.
Figure 4:
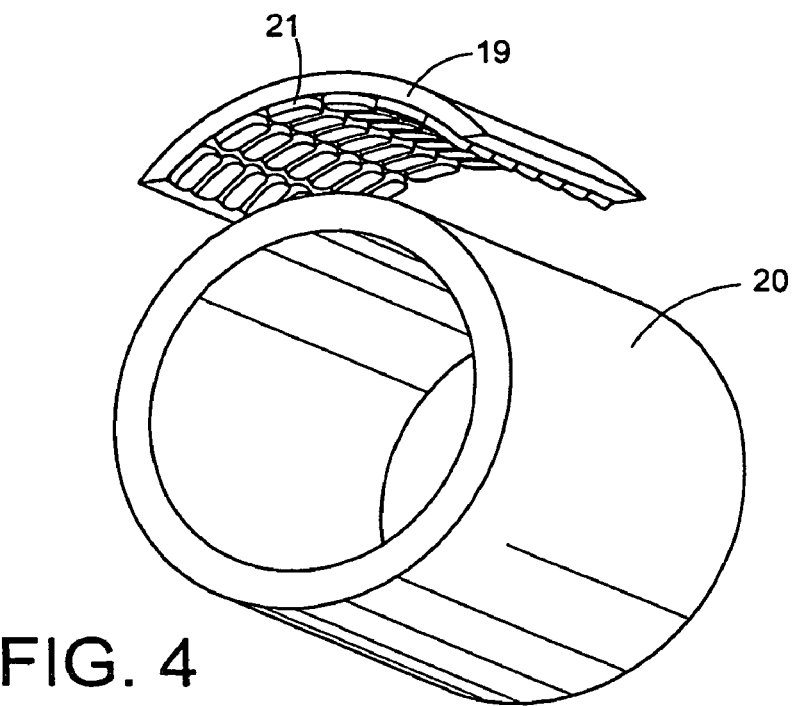
FIG. 4 illustrates a flexible EMAT that is adapted for generation and detection of SH waves in non-planar electrically conducting materials.

Illustrated in FIG. 4 is a conformable-flexible multiple-pole magnet array 19, which may be used with other electrical components known in the art to form an EMAT that generates SH waves in a curved metallic component, for example but not for limitation, such as a steel pipe 20. The magnets 1 contain magnetic poles 21 and interconnecting links or segments, both of which can be comprised of either ferromagnetic or non-ferromagnetic material. The flexible multiple-pole magnet array 19 may be fabricated and assembled so that it conforms to the curvature of the material structure to which the EMAT will be applied to perform the desired test.

One method of fabricating the flexible multiple-pole magnet array is to mold a conformable-flexible compound, for example but not for limitation, such as silicone rubber, impregnated or filled with particles of ferromagnetic material 14, for example but not for limitation, such as iron. In this embodiment, at least one RF coil 4 comprising insulated electrical conductors is installed between the poles 21 to generate magnetic fields 2 that are perpendicular to the faces of each magnetic pole 21 when the RF coil 4 is energized by electrical currents.

In another embodiment, the conformable-flexible compound is impregnated with permanent magnet material 14, for example but not for limitation, such as neodymium iron boron. In this embodiment, the magnetic poles 21 may be magnetized prior to use to provide static magnetic fields 2 that are perpendicular to the faces of each magnetic pole 21.

Figure 5:
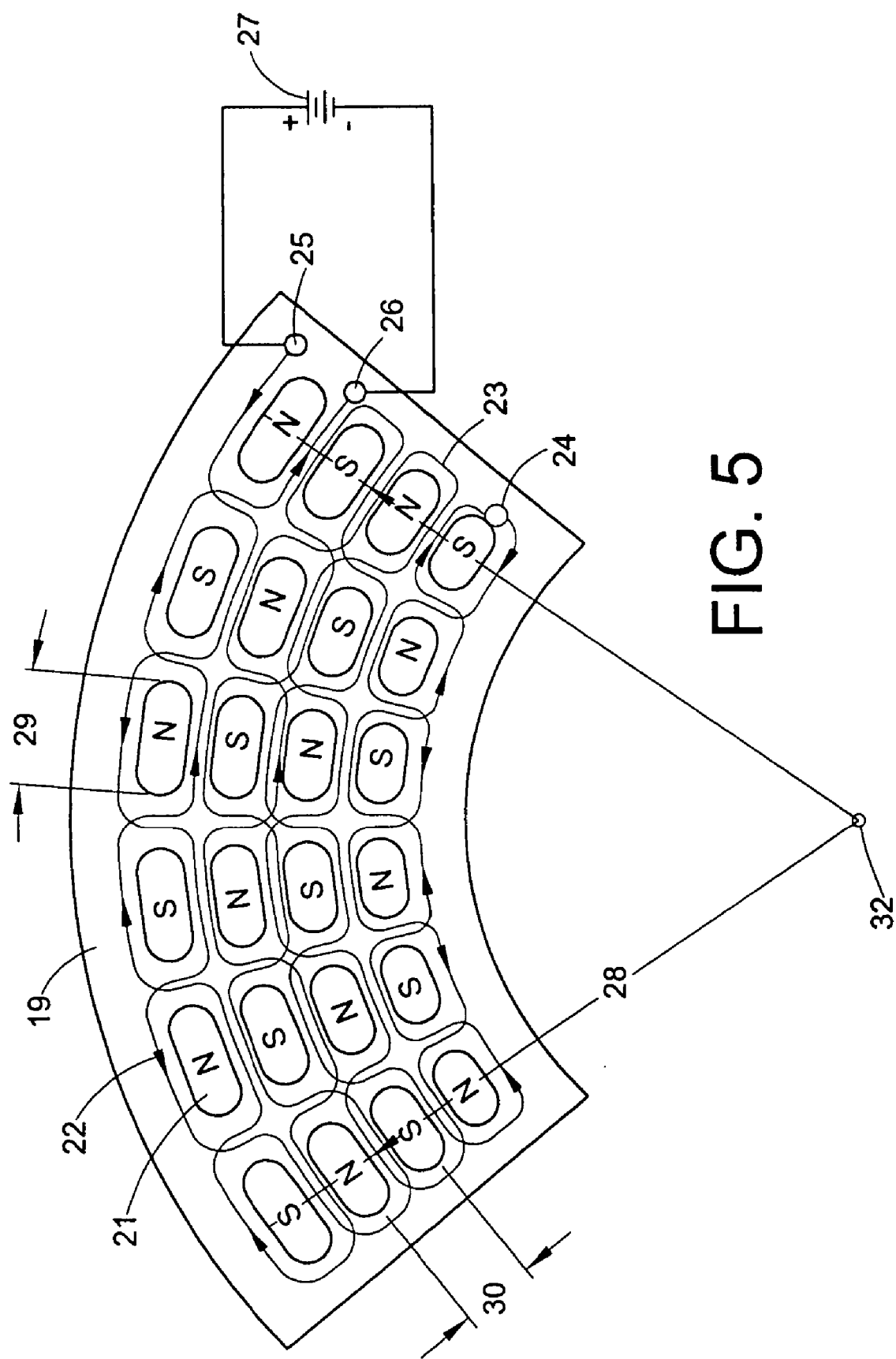
FIG. 5 illustrates a flexible multiple-pole magnet array comprising mechanically and magnetically linked magnetic pole pieces and distributed windings of electrical conductors comprising an RF coil.

Illustrated in FIG. 5 is a planar view of a flexible, multiple-pole magnet array 19 that may be used with other electrical components for generation of SH waves 11. It is comprised in part of an array of north (N) and south (S) magnetic poles 21, which are connected mechanically and magnetically by linkages of magnetic material (not shown). One such embodiment uses a flexible hydrocarbon containing material, for example but not for limitation, an elastomer such as silicone rubber that is impregnated with particles of ferromagnetic materials or permanent magnetic materials, such as iron or neodymium iron boron compounds respectively. This mixture may be molded into flexible multiple-pole magnet arrays 19 containing one or more magnetic poles 21 in a variety of configurations, which provide enhancements in EMAT performance, including increased SH wave 11 intensity, SH wave 11 steering and focusing.

The flexible multiple-pole magnet array 19, may comprise layers of insulated conductor 22 and second insulated conductor 23, which may be woven between the magnetic poles 21 so that they provide magnetization in a direction that has a predominant magnetic field vector component perpendicular to the magnetic pole 21 face and the surface of the test material 3. The insulated conductor layer 22 and second insulated conductor layer 23 may be placed between the magnetic poles 21 in a pattern that produces opposite polarity in adjacent magnetic poles 21 when the insulated conductor layer 22 and second insulated conductor layer 23 are energized by a current source 27. When the flexible multiple-pole magnet array is used as a permanent magnet array, the insulated conductor layer 22 and second insulated conductor layer 23 may be absent, or removed, to provide increased flexibility and conformity to the test material 3 surface.

Assembly of the magnet may include the insertion of insulated conductor layer 22 between the poles, followed by the insertion of a second insulated conductor layer 23, part of which overlays insulated conductor layer 22. When insulated conductor layer 22 and second insulated conductor layer 23 are connected electrically at junction 24, the flexible multiple-pole magnet array's 19 interior magnetic poles 21 are effectively encircled by two interwoven insulated conductors (insulated conductor layer 22 and second insulated conductor layer 23) that carry electrical current in the same direction when energized at terminals 25 and 26 by current source 27 which in one embodiment is a direct current source. Additional pairs of conductor layers similar to insulated conductor layer 22 and second insulated conductor layer 23 may be installed over insulated conductor layer 22 and second insulated conductor layer 23 and connected in series or in parallel with said layers to provide increased magnetizing current and increased magnetic field normal to each magnetic pole 21 face.

The array of magnetic poles 21 may be shaped and positioned so that they collectively produce a focusing SH wave 11 at an approximate radial distance 28, as indicated in FIG. 5. The width 29 of each magnetic pole 21 may be a function of its radial distance 28 from the focal point 32, increasing in proportion to the radial distance 28 from the center of the magnet 1. The distance 30 between magnetic poles 21 in conjunction with the excitation frequency of the RF coil 4 determines the angle of the SH wave 11 with respect to the normal direction to the test material 3 surface. A decrease in distance 30, or a decrease in RF excitation frequency within the functional range, results in an increase in the angle of the SH wave 11 with respect to the surface of the test material 3, that is, the test substrate.

A variation in the distance 30 between adjacent magnetic poles 21 as a function of radial distance 28 causes a change in the vertical width of the SH wave 11. For example, a decrease in distance between two magnetic poles 21 that is proportional to the radial distance 28 to the magnetic pole 21 pair can result in a decrease in the vertical width of the SH wave 11 and greater resolution in detecting defects. Similarly, two or more flexible multiple-pole magnet arrays 19, each having a different radial distance 28 between magnetic poles 21, may be arranged in tandem so that they will have approximately the same focal point 32 when operated within the prescribed range of frequencies.

Figure 6A:
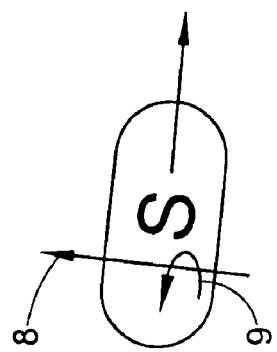
FIG. 6A illustrates the eddy currents and magnetic fields associated with one magnetic pole face in the array of FIG. 6.
Figure 6:
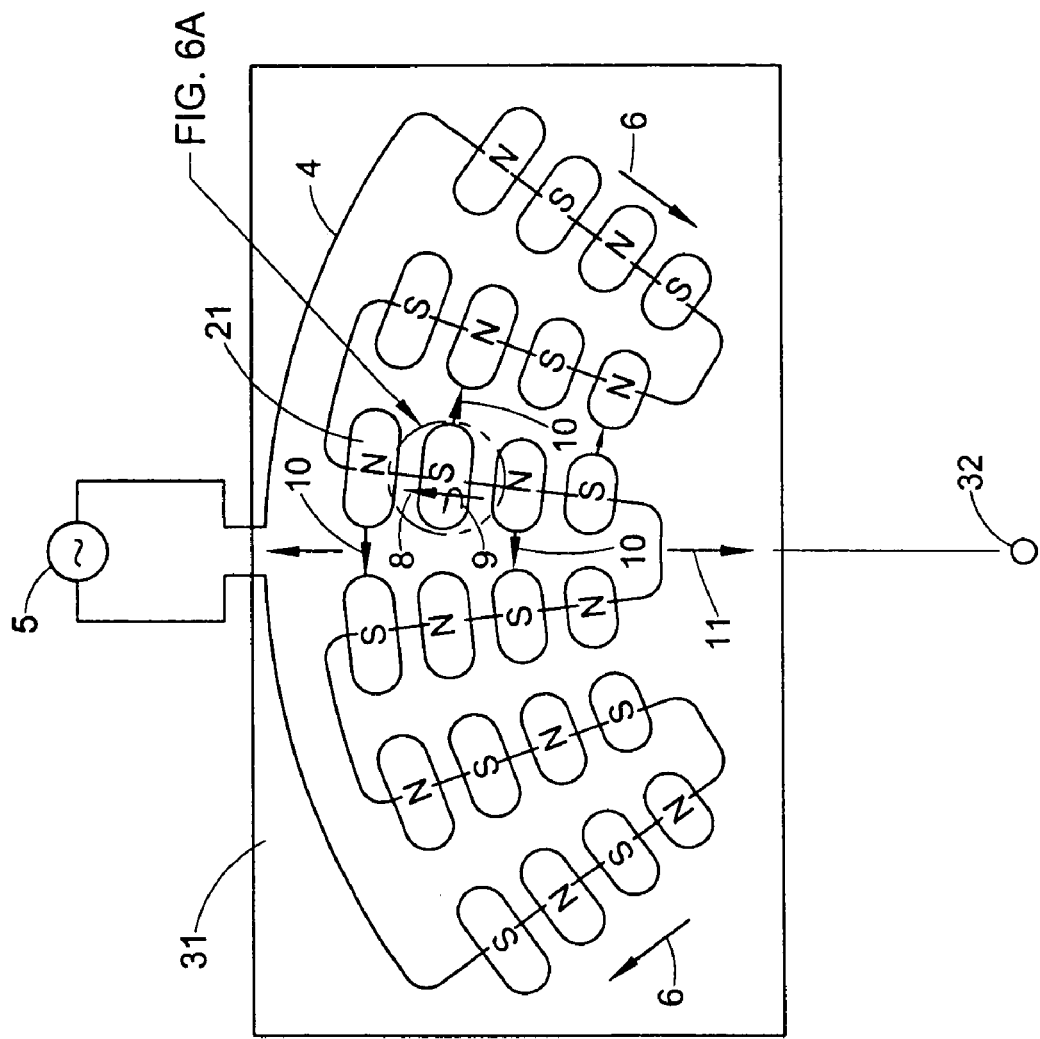
FIG. 6 illustrates a flexible RF coil placed in close proximity to the magnetic pole faces of the flexible multiple-pole magnet array.

The RF coils 4 illustrated in FIG. 6 are comprised of electrical conductors attached to a flexible substrate 31 of electrically insulating material. The RF coils 4 are attached to the magnetic pole 21 faces, so that they are in close proximity to the test material 3. When the alternating voltage of an alternating power source 5 is applied to the RF coils 4, Lorentz forces 10 are applied to the test material 3 at an instant in time when the voltage is positive in the directions as indicated in FIG. 6 and FIG. 6A. The Lorentz forces 10 are in diametrically opposite directions between upper and lower adjacent magnetic poles 21 in each column of magnetic poles 21. This is attributed to the opposing polarity of adjacent magnetic poles 21. As, induced eddy currents 8 with associated magnetic fields 9 reverse direction under adjacent columns of magnetic poles 21, the Lorenz forces 10 are in the same direction in a given row of magnetic poles 21. These alternating forces add to produce an SH wave 11 traveling toward the focal point 32.

Figure 7:
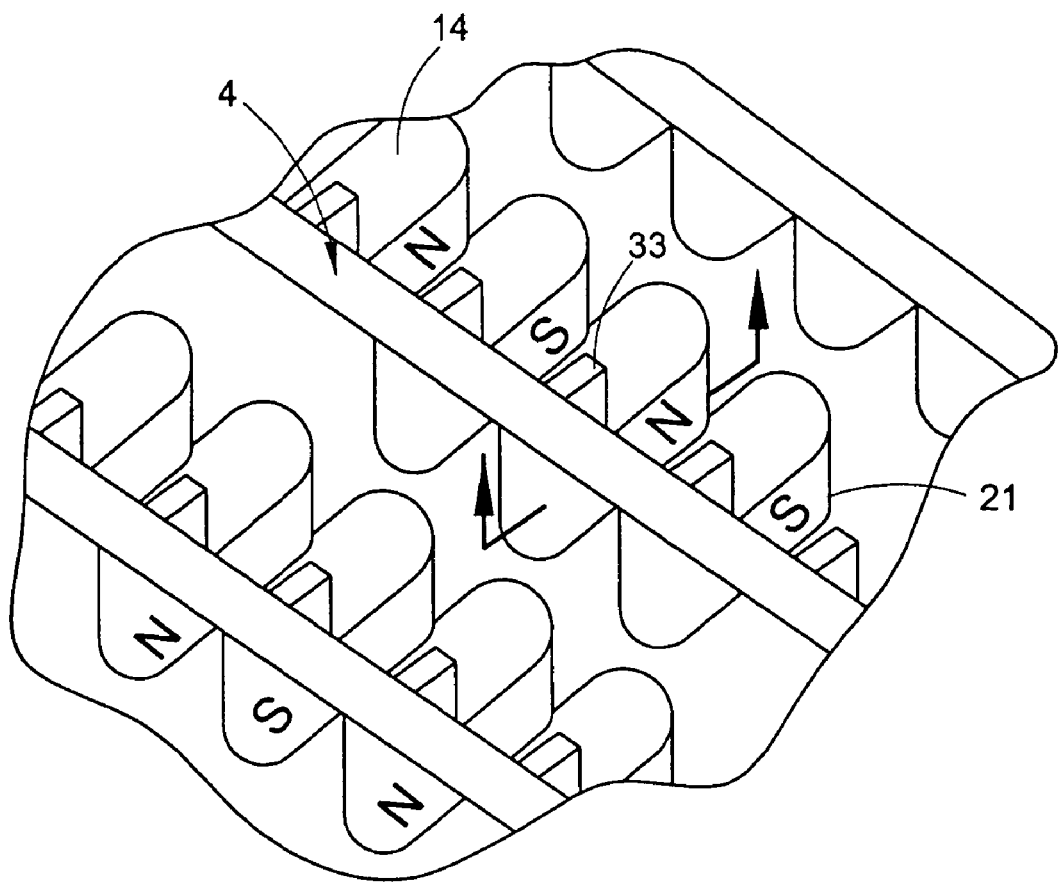
FIG. 7 illustrates a flexible RF coil embedded in the magnetic pole faces of an array of flexible magnets.
Figure 7A:
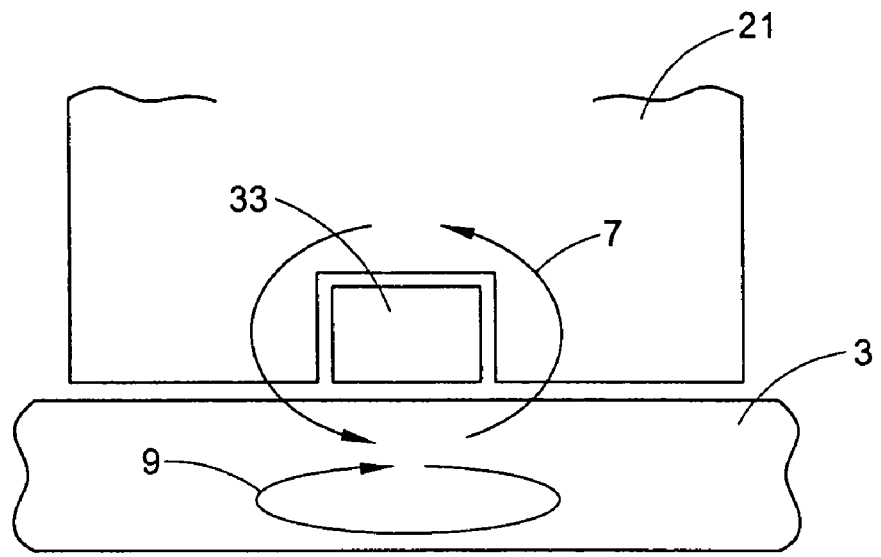
FIG. 7A illustrates a cross-section of the embedded RF coil conductor along line A–A' of FIG. 7.

The magnetic poles 21 of the multiple-pole electromagnet array 19 may provide for an increase in the electromagnetic coupling of the RF conductors 33 to the test material. This electromagnetic coupling can be further increased by embedding RF conductors 33 within the magnetic poles 21 of the ferromagnetic material 14, as illustrated in FIG. 7. As shown in FIG. 7A, the embedded RF conductors 33 and the magnetic poles 21 may be closer to the test material 3, thereby increasing the quantity of alternating magnetic field 9 that penetrates the test material 3. The amplitude of the induced eddy currents 8 that are induced by the alternating fields 7 is increased, which in turn increases the intensity of Lorentz forces 10 and the resultant SH wave 11 in the test material.

It will be understood that the embodiments described herein are merely exemplary and that a person skilled in the art may make many variations and modifications without departing from the spirit and scope of the invention. All such modifications and variations are intended to be included within the scope of the invention as described herein. It should be understood that the embodiments described above are not only in the alternative, but can be combined.

We claim:

1. An electromagnetic acoustic transducer adapted to conform to the surface of a non-planar test substrate; wherein the electromagnetic acoustic transducer is adapted for generation and detection of ultrasonic acoustic waves and comprises an array of flexible multiple-pole magnets conformable to the non-planar test substrate surface, wherein the magnets contain magnetic poles and interconnecting segments; and wherein the magnetic poles are disposed in a plurality of rows.

2. The electromagnetic acoustic transducer of claim 1 wherein the flexible multiple-pole magnet array comprises a flexible compound containing particles of ferromagnetic material, wherein at least one electrical conductor is disposed between the magnetic poles capable of generating magnetic fields perpendicular to the faces of each magnetic pole when conducting current.

3. The electromagnetic acoustic transducer of claim 2 wherein at least one layer of electrical conductor is disposed between the magnetic poles to provide magnetization in a direction that has a predominant magnetic field vector component perpendicular to the magnetic pole face and the surface of the test substrate.

4. The electromagnetic acoustic transducer of claim 3 wherein the electrical conductor is disposed between the magnetic poles in a pattern to produce opposite polarity in adjacent magnetic poles when the electrical conductor is conducting current.

5. The electromagnetic acoustic transducer of claim 3 wherein a layer of a second electrical conductor at least in part overlays the at least one electrical conductor layer and is connected electrically thereto, wherein the magnetic poles interior to the electrical conductor and the second electrical conductor are effectively encircled by two electrical conductors that carry electrical current in the same direction when conducting current.

6. The electromagnetic acoustic transducer of claim 5 wherein at least one additional pair of electrical conductor layers is disposed over the at least one electrical conductor layer and second electrical conductor layer and is connected in series or in parallel with said at least one electrical conductor layer and said second electrical conductor layer.

7. The electromagnetic acoustic transducer of claim 1 wherein the flexible multiple-pole magnet array comprises a flexible compound containing particles of permanent magnet material, wherein the magnetic poles are optionally magnetized to provide static magnetic fields perpendicular to the face of each magnetic pole.

8. The electromagnetic acoustic transducer of claim 1 wherein each row has a radius of curvature about at least one focal point capable of focusing a generated sound wave in the test substrate.

9. The electromagnetic acoustic transducer of claim 8 wherein the distance between adjacent magnetic poles varies as a function of the radial distance from the focal point.

10. The electromagnetic acoustic transducer of claim 8 comprising at least two flexible multiple-pole magnet arrays in tandem wherein each array has a different radial distance between magnetic poles but approximately the same focal point, and wherein the at least two arrays are capable of effecting approximately the same sound wave angle.

11. The electromagnetic acoustic transducer of claim 8 wherein the flexible multiple-pole magnet array has RF conductors embedded in grooves which lie across the magnetic pole faces and are collinear with radial projections from the focal point.

12. The electromagnetic acoustic transducer of claim 1 wherein the magnets comprise iron.

13. The electromagnetic acoustic transducer of claim 7 wherein the magnets comprise neodymium iron boron.

14. The electromagnetic acoustic transducer of claim 2 wherein the flexible compound is an elastomer.

15. The electromagnetic acoustic transducer of claim 14 wherein the elastomer comprises silicone rubber.

16. The electromagnetic acoustic transducer of claim 7 wherein the flexible compound is an elastomer.

17. The electromagnetic acoustic transducer of claim 16 wherein the elastomer comprises silicone rubber.

18. A method of interrogating a test substrate having a non-planar surface using the electromagnetic acoustic transducer of claim 1 comprising:
  conforming the electromagnetic acoustic transducer to the surface of the test substrate in monitoring proximity to the surface,
  generating a sound wave by interaction of fields from the electromagnetic acoustic transducer magnets and an electrical conductor, and,
  detecting at least one characteristic of the sound wave reflected by the test substrate.

* * * * *